United States Patent [19]

Anthony et al.

[11] Patent Number: 5,221,316

[45] Date of Patent: Jun. 22, 1993

[54] FUNGICIDES

[75] Inventors: Vivienne M. Anthony, Maidenhead; John M. Clough, Marlow; Paul DeFraine, Wokingham; Christopher R. A. Godfrey, Bracknell; Patrick J. Crowley, Crowthorne; Kenneth Anderton, Bury, all of England

[73] Assignee: Imperial Chemical Industries PLC, London, England

[21] Appl. No.: 836,970

[22] Filed: Feb. 19, 1992

Related U.S. Application Data

[62] Division of Ser. No. 292,308, Dec. 30, 1988, Pat. No. 5,112,386, which is a division of Ser. No. 39,401, Apr. 17, 1987, Pat. No. 4,826,531.

[30] Foreign Application Priority Data

Apr. 17, 1986 [GB] United Kingdom ............... 8609456
Jan. 26, 1987 [GB] United Kingdom ............... 8701627

[51] Int. Cl.$^5$ .................. A01N 43/40; A01N 43/50; A61K 31/505; C07D 239/02
[52] U.S. Cl. .................. 504/210; 514/252; 514/269; 514/272; 514/273; 514/274; 544/300; 544/310; 544/316; 544/317; 544/318; 544/319; 544/320; 544/321; 544/322; 544/324; 544/328; 544/331; 544/333; 544/360; 504/242; 504/243; 504/235
[58] Field of Search .............. 71/92; 514/252, 269, 514/272, 273, 274; 544/300, 310, 316, 317, 318, 319, 320, 321, 322, 324, 328, 331, 333, 360

[56] References Cited

U.S. PATENT DOCUMENTS 4,620,008 10/1986 Brandstrom et al. ............... 546/290

FOREIGN PATENT DOCUMENTS 0104690 4/1984 European Pat. Off. .
0203606 3/1986 European Pat. Off. .
0203608 3/1986 European Pat. Off. .
0178826 4/1986 European Pat. Off. .

OTHER PUBLICATIONS

Chem. Abstracts, (1972) 101(21): 191812c; 70(21:96597u; and 55:247409 (1960).
J. Org. Chem., 49:22,4287-90 (1984) Chem. Ber., 102:3, 914-25 (1969).
Chemical Abstracts Online registry.

Primary Examiner—Johann Richter
Attorney, Agent, or Firm—Cushman, Darby & Cushman

[57] ABSTRACT

Acrylic acid derivatives having the formula (I):

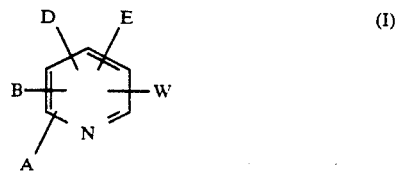

and stereoisomers thereof, wherein W is $R^1O_2C$—C=CH—$ZR^2$, $R^1$ and $R^2$ are alkyl or fluoroalkyl groups, and Z is oxygen or sulphur; A, B, D and E are hydrogen, halogen, hydroxy or optionally substituted alkyl, alkoxy, aralkyl, arylalkoxy, alkenyl, alkynyl, aryl, aryloxy, arylthio, heteroaryloxy, heteroarylthio, acyloxy, amino, arylazo or acylamino, nitro, cyano, —$CO_2R^3$, —$CONR^3R^4$, —$COR^3$, —$CR^3$=$NR^4$, —N=$CR^3R^4$ or —$S(O)_nR^3$ groups; any two of the groups A, B, D and E, when they are in adjacent positions on the ring, optionally join to form a fused ring, n is 0, 1 or 2; and $R^3$ and $R^4$ are hydrogen, alkyl, cycloalkyl, cycloalkylalkyl, alkenyl, alkynyl or optionally substituted aryl or aralkyl; and metal complexes thereof. These compounds are useful as fungicides, insecticides, nematicides or plant growth regulators.

15 Claims, No Drawings

FUNGICIDES

This is a division of application Ser. No. 07/292,308, filed Dec. 30, 1988, now U.S. Pat. No. 5,112,386, which is a divisional of Ser. No. 07/039,401, filed Apr. 17, 1987, now U.S. Pat. No. 4,826,531.

This invention relates to derivatives of acrylic acid useful in agriculture (especially as fungicides but also as insecticices, nematicides and plant growth regulators), to processes for preparing them, to agricultural compositions containing them, and to methods of using them to combat fungi, especially fungal infections in plants, to kill or control insect and nematode pests and to regulate plant growth.

The invention provides a compound having the general formula (I):

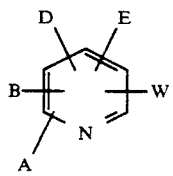

and stereoisomers thereof, wherein W is $R^1O_2C\text{—}C=CH\text{—}ZR^2$, wherein $R^1$ and $R^2$, which are the same or different, are alkyl or fluoroalkyl groups, and Z is either an oxygen or sulphur atom; A, B, D and E, which are the same or different, are hydrogen or halogen atoms, or hydroxy, optionally substituted alkyl, optionally substituted alkoxy, optionally substituted aralkyl, optionally substituted arylalkoxy, optionally substituted alkenyl, optionally substituted alkynyl, optionally substituted aryl, optionally substituted aryloxy, optionally substituted arylthio, optionally substituted heteroaryloxy, optionally substituted heteroarylthio, optionally substituted acyloxy, optionally substituted amino, optionally substituted arylazo, optionally substituted acylamino, nitro, cyano, $\text{—}CO_2R^3$, $\text{—}CONR^3R^4$, $\text{—}COR^3$, $\text{—}CR^3=NR^4$, $\text{—}N=CR^3R^4$ or $\text{—}S(O)_nR^3$ groups; any two of the groups A, B, D and E, when they are in adjacent positions on the ring, optionally join to form a fused ring, either aromatic or aliphatic, optionally containing one or more heteroatoms; n is 0, 1 or 2; and $R^3$ and $R^4$, which are the same or different, are hydrogen atoms or alkyl, cycloalkyl, cycloalkylalkyl, alkenyl, alkynyl, optionally substituted aryl or optionally substituted aralkyl groups; and metal complexes thereof.

The compounds of the invention contain at least one carbon-carbon double bond, and are sometimes obtained in the form of mixtures of geometric isomers. However, these mixtures can be separated into individual isomers, and this invention embraces such isomers, and mixtures thereof in all proportions including those which consist substantially of the (Z)-isomer and those which consist substantially of the (E)-isomer.

The individual isomers which result from the unsymmetrically substituted double bond of the substituent W are identified by the commonly used terms "E" and "Z". These terms are defined according to the Cahn-Ingold-Prelog system which is fully described in the literature (see, for example, J March, "Advanced Organic Chemistry", 3rd edition, Wiley-Interscience, page 109 et seq).

Usually one isomer is more fungicidally active than the other, the more active isomer being the one in which the group $\text{—}ZR^2$ on the W substituent ($R^1O_2C\text{—}C=CH\text{—}ZR^2$) is on the same side of the double bond as the pyridine ring. In the case of the compounds of the present invention this is the (E)-isomer. These isomers form a preferred embodiment of the invention.

In the compounds of formula (I), alkyl groups and the alkyl moiety of alkoxy groups can be in the form of straight or branched chains, and preferably contain 1 to 6 carbon atoms, more preferably 1 to 4 carbon atoms. Examples are methyl, ethyl, propyl (n-and iso-propyl) and butyl (n-, sec-, iso- and tert-butyl). Cycloalkyl groups, which are preferably $C_{3-6}$ cycloalkyl groups, include cyclohexyl and cycloalkylalkyl groups, which are preferably $C_{3-6}$ cycloalkyl($C_{1-4}$)alkyl groups, include cyclopropylethyl. Alkenyl and alkynyl groups preferably contain 2 to 6, more preferably 2 to 4, carbon atoms in the form of straight or branched chains. Examples are ethyenyl, allyl and propargyl. Aryl is preferably phenyl and aralkyl is preferably benzyl, phenylethyl or phenyl-n-propyl. Optionally substituted alkyl includes, in particular, haloalkyl, hydroxyalkyl, alkoxyalkyl and optionally substituted aryloxyalkyl (especially optionally substituted phenoxyalkyl) and optionally substituted heteroaryloxyalkyl (especially pyridinyl- and pyrimidinyloxyalkyl); optionally substituted alkenyl includes optionally substituted phenylalkenyl, especially optionally substituted phenylethenyl; and optionally substituted arylalkoxy includes optionally substituted benzyloxy.

Substituents which may be present in any optionally substituted aryl or heteroaryl moiety include one or more of the following; halogen (especially fluorine, chlorine and bromine), hydroxy, $C_{1-4}$ alkyl (especially methyl and ethyl), ($C_{1-4}$) alkoxy (especially methoxy), halo ($C_{1-4}$) alkyl (especially trifluoromethyl), halo $C_{1-4}$ alkoxy (especially trifluoromethoxy), $C_{1-4}$ alkylthio (especially methylthio) $C_{1-4}$ alkoxy ($C_{1-4}$)alkyl, $C_{3-6}$ cycloalkyl, $C_{3-6}$ cycloalkyl-($C_{1-4}$) alkyl, aryl (especially phenyl), aryloxy (especially phenyloxy), aryl ($C_{1-4}$)alkyl (especially benzyl, phenylethyl and phenyl n-propyl), aryl ($C_{1-4}$)alkoxy (especially benzyloxy), aryloxy ($C_{1-4}$)alkyl (especially phenyloxymethyl), acyloxy (especially acetyloxy and benzoyloxy), cyano, thiocyanato, nitro, $\text{—}NR'R''$, $\text{—}NHCOR'$, $\text{—}NHCONR'R''$, $\text{—}CONR'R''$, $\text{—}COOR'$, $\text{—}OSO_2R'$, $\text{—}SO_2R'$, $\text{—}COR'$, $\text{—}CR'=NR''$ or $\text{—}N=CR'R''$ in which R' and R'' are independently hydrogen, $C_{1-4}$ alkyl, $C_{1-4}$ alkoxy, $C_{1-4}$ alkylthio, $C_{3-6}$ cycloalkyl, $C_{3-6}$ cycloalkyl($C_{1-4}$)-alkyl, phenyl or benzyl, the phenyl and benzyl groups being optionally substituted with halogen, $C_{1-4}$ alkyl or $C_{1-4}$ alkoxy.

Optionally substituted amino, acylamino and acyloxy groups include the groups $\text{—}NR'R''$, $\text{—}NHCOR'$ and $\text{—}OCOR'$ in which R' and R'' are as defined above.

Compounds of formula (I) which are of particular interest are those in which A, B, D and E are selected from the group consisting of hydrogen, halogen (especially fluorine, chlorine and bromine), $C_{1-4}$ alkyl (especially methyl and ethyl), trifluoromethyl, $C_{1-4}$ alkoxy (especially methoxy), trifluoromethoxy, aralkyl (especially phenyl($C_{1-4}$)alkyl including benzyl, phenylethyl and phenyl n-propyl), aralkenyl (especially phenylethenyl, which may be the (E)- or (Z)-isomer), $\text{—}COOR^3$, in which R is $C_{1-4}$ alkyl (especially methyl or ethyl), $C_{3-4}$ alkenyl (especially allyl) or aryl (especially phenyl), aryloxy (especially phenoxy), arylthio (especially phenyloxy and phenylthio), heteroaryloxy, heteroarylthio (especially pyridinyl-, pyrimidinyl-, pyrazinyland benzoxazolyl-oxy and thio), benzyloxy, benzylthio and phenyloxymethyl, all of which may carry one or more ring substituents such as halogen (especially fluorine, chlorine and bromine), cyano, nitro, $C_{1-4}$ alkyl (especially methyl), $C_{1-4}$ alkoxy (especially methoxy), trifluoromethyl and trifluoro-methoxy.

It is preferred that at least one of A, B, D and E is a group other than hydrogen and that it is in a position on the pyridine ring ortho to the substituent W. Thus when W is in the 2- or 4-position of the pyridine ring, one of A to E is in the 3-position, and when W is in the 3-position which is preferred, one of A to E is in the 2-(preferably) or 4-position. When any two of A, B, D and E are in adjacent positions on the pyridine ring they may join to form a fused ring either aromatic or aliphatic, optionally containing one or more heteroatoms, such as a fused benzene ring.

It is further preferred that at least one of $R^1$ and $R^2$ is methyl, preferably $R^2$, and even more preferably, that both are methyl.

It is still further preferred that Z (in the substituent W) is oxygen.

Thus in a particular embodiment of the invention, there is included the compound (II)

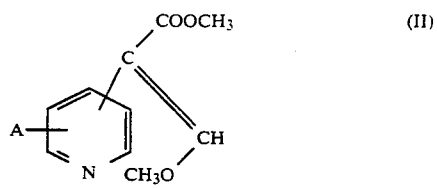

preferably the (E)-isomer, wherein A, which is in a position ortho to the acrylate group, is phenoxy (optionally substituted with one or more of fluoro, chloro, bromo, methyl, methoxy, trifluoromethyl, trifluoromethoxy, cyano or nitro), phenylthio, benzyl, phenylethyl, phenylethenyl (either the (E)- or (Z)-isomer), benzyloxy, phenyloxymethyl, benzylthio, —$COOR^3$ (in which $R^3$ is methyl, ethyl, allyl or phenyl), pyridinyl-, pyrimidinyl- or pyrazinyl-oxy or -thio (optionally substituted with chloro, bromo or trifluoromethyl), or benzoxazolyl-oxy or -thio.

Examples of the compounds of the invention are shown in Table I. In this Table "Ph" stands for phenyl (ie $C_6H_5$).

TABLE I

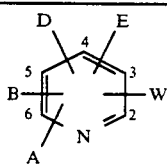

(I)

| Compound No | W | A | B | D | E | Melting Point (°C.) | olefinic* |
|---|---|---|---|---|---|---|---|
| 1 | 2-((E)-CH₃O₂C.C=CH.OCH₃) | 3-PhO— | H | H | H | Oil | 7.56 |
| 2 | 2-((E)-CH₃O₂C.C=CH.OCH₃) | 3-(4'-chlorophenoxy)- | H | H | H | | |
| 3 | 2-((E)-CH₃O₂C.C=CH.OCH₃) | 3-(4'-fluorophenoxy)- | H | H | H | | |
| 4 | 2-((E)-CH₃O₂C.C=CH.OCH₃) | 3-(4'-bromophenoxy)- | H | H | H | | |
| 5 | 2-((E)-CH₃O₂C.C=CH.OCH₃) | 3-(4'-methylphenoxy)- | H | H | H | | |
| 6 | 2-((E)-CH₃O₂C.C=CH.OCH₃) | 3-(4'methoxyphenoxy)- | H | H | H | | |
| 7 | 2-((E)-CH₃O₂C.C=CH.OCH₃) | 3-(4'-trifluoromethyl-phenoxy)- | H | H | H | | |
| 8 | 2-((E)-CH₃O₂C.C=CH.OCH₃) | 3-(4'trifluoromethoxy-phenoxy)- | H | H | H | | |
| 9 | 2-((E)-CH₃O₂C.C=CH.OCH₃) | 3-(3'-chlorophenoxy)- | H | H | H | | |
| 10 | 2-((E)-CH₃O₂C.C=CH.OCH₃) | 3-PhS— | H | H | H | | |
| 11 | 2-((E)-CH₃O₂C.C=CH.OCH₃) | 3-PhCH₂— | H | H | H | | |
| 12 | 2-((E)-CH₃O₂C.C=CH.OCH₃) | 3-PhCH₂CH₂— | H | H | H | | |
| 13 | 2-((E)-CH₃O₂C.C=CH.OCH₃) | 3-(E-CH=CHPh)— | H | H | H | | |
| 14 | 2-((E)-CH₃O₂C.C=CH.OCH₃) | 3-(Z-CH=CHPh)— | H | H | H | | |
| 15 | 3-((E)-CH₃O₂C.C=CH.OCH₃) | 2-PhO— | H | H | H | 121-3 | 7.6 |
| 16 | 3-((E)-CH₃O₂C.C=CH.OCH₃) | 2-(4'-chlorophenoxy)- | H | H | H | 113-115.6 | 7.58 |
| 17 | 3-((E)-CH₃O₂C.C=CH.OCH₃) | 2-(4'-fluorophenoxy)- | H | H | H | 116-118 | 7.60 |
| 18 | 3-((E)-CH₃O₂C.C=CH.OCH₃) | 2-(4'-bromophenoxy)- | H | H | H | 89.8-90.5 | 7.44 |
| 19 | 3-((E)-CH₃O₂C.C=CH.OCH₃) | 2-(4'-methylphenoxy)- | H | H | H | 105.2-106.8 | 7.59 |
| 20 | 3-((E)-CH₃O₂C.C=CH.OCH₃) | 2-(4'-methoxyphenoxy)- | H | H | H | 105.6-106.6 | 7.60 |
| 21 | 3-((E)-CH₃O₂C.C=CH.OCH₃) | 2-(4'-trifluoromethyl-phenoxy)- | H | H | H | Oil | 7.50 |
| 22 | 3-((E)-CH₃O₂C.C=CH.OCH₃) | 2-(4'-trifluoromethoxy-phenoxy)- | H | H | H | | |
| 23 | 3-((E)-CH₃O₂C.C=CH.OCH₃) | 2-(3'-chlorophenoxy)- | H | H | H | Oil | 7.58 |
| 24 | 3-((E)-CH₃O₂C.C=CH.OCH₃) | 2-PhS— | H | H | H | | |
| 25 | 3-((E)-CH₃O₂C.C=CH.OCH₃) | 2-PhCH₂— | H | H | H | | |
| 26 | 3-((E)-CH₃O₂C.C=CH.OCH₃) | 2-PhCH₂CH₂— | H | H | H | | |
| 27 | 3-((E)-CH₃O₂C.C=CH.OCH₃) | 2-((E)-CH=CHPh)— | H | H | H | | |
| 28 | 3-((E)-CH₃O₂C.C=CH.OCH₃) | 2-((Z)-CH=CHPh)— | H | H | H | | |
| 29 | 3-((E)-CH₃O₂C.C=CH.OCH₃) | 4-PhO— | H | H | H | Gum | 7.64 |
| 30 | 3-((E)-CH₃O₂C.C=CH.OCH₃) | 4-(4'-chlorophenoxy)- | H | H | H | | |
| 31 | 3-((E)-CH₃O₂C.C=CH.OCH₃) | 4-(4'-fluorophenoxy)- | H | H | H | | |
| 32 | 3-((E)-CH₃O₂C.C=CH.OCH₃) | 4-(4'-bromophenoxy)- | H | H | H | | |
| 33 | 3-((E)-CH₃O₂C.C=CH.OCH₃) | 4-(4'-methylphenoxy)- | H | H | H | | |
| 34 | 3-((E)-CH₃O₂C.C=CH.OCH₃) | 4-(4'-methoxyphenoxy)- | H | H | H | | |
| 35 | 3-((E)-CH₃O₂C.C=CH.OCH₃) | 4-(4'-trifluoromethyl-phenoxy)- | H | H | H | | |
| 36 | 3-((E)-CH₃O₂C.C=CH.OCH₃) | 4-(4'-trifluoromethoxy- | H | H | H | | |

TABLE I-continued (I)

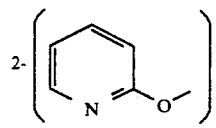

| Compound No | W | A | B | D | E | Melting Point (°C.) | olefinic* |
|---|---|---|---|---|---|---|---|
| 37 | 3-((E)-CH₃O₂C.C=CH.OCH₃) | 4-(3'-chlorophenoxy)- | H | H | H | | |
| 38 | 3-((E)-CH₃O₂C.C=CH.OCH₃) | 4-PhS— | H | H | H | | |
| 39 | 3-((E)-CH₃O₂C.C=CH.OCH₃) | 4-PhCH₂— | H | H | H | | |
| 40 | 3-((E)-CH₃O₂C.C=CH.OCH₃) | 4-PhCH₂CH₂— | H | H | H | | |
| 41 | 3-((E)-CH₃O₂C.C=CH.OCH₃) | 4-((E)-CH=CHPh)— | H | H | H | | |
| 42 | 3-((E)-CH₃O₂C.C=CH.OCH₃) | 4-((Z)-CH=CHPh)— | H | H | H | | |
| 43 | 4-((E)-CH₃O₂C.C=CH.OCH₃) | 3-PhO— | H | H | H | Oil | 7.50 |
| 44 | 4-((E)-CH₃O₂C.C=CH.OCH₃) | 3-(4'-chlorophenoxy)- | H | H | H | | |
| 45 | 4-((E)-CH₃O₂C.C=CH.OCH₃) | 3-(4'-fluorophenoxy)- | H | H | H | | |
| 46 | 4-((E)-CH₃O₂C.C=CH.OCH₃) | 3-(4'-bromophenoxy)- | H | H | H | | |
| 47 | 4-((E)-CH₃O₂C.C=CH.OCH₃) | 3-(4'-methylphenoxy)- | H | H | H | | |
| 48 | 4-((E)-CH₃O₂C.C=CH.OCH₃) | 3-(4'-methoxyphenoxy)- | H | H | H | | |
| 49 | 4-((E)-CH₃O₂C.C=CH.OCH₃) | 3-(4'-trifluoromethyl-phenoxy)- | H | H | H | | |
| 50 | 4-((E)-CH₃O₂C.C=CH.OCH₃) | 3-(4'-trifluoromethoxy-phenoxy)- | H | H | H | | |
| 51 | 4-((E)-CH₃O₂C.C=CH.OCH₃) | 3-(3'-chlorophenoxy)- | H | H | H | | |
| 52 | 4-((E)-CH₃O₂C.C=CH.OCH₃) | 3-PhS— | H | H | H | | |
| 53 | 4-((E)-CH₃O₂C.C=CH.OCH₃) | 3-PhCH₂— | H | H | H | | |
| 54 | 4-((E)-CH₃O₂C.C=CH.OCH₃) | 3-PhCH₂CH₂— | H | H | H | | |
| 55 | 4-((E)-CH₃O₂C.C=CH.OCH₃) | 3-((E)-CH=CHPh)— | H | H | H | | |
| 56 | 4-((E)-CH₃O₂C.C=CH.OCH₃) | 3-((Z)-CH=CHPh)— | H | H | H | | |
| 57 | 3-((E)-CH₃O₂C.C=CH.OCH₃) | 2-(3'-fluorophenoxy)- | H | H | H | Oil | 7.59 |
| 58 | 3-((E)-CH₃O₂C.C=CH.OCH₃) | 2-(3'-methylphenoxy)- | H | H | H | 113–5 | 7.55 |
| 59 | 3-((E)-CH₃O₂C.C=CH.OCH₃) | 2-(2'-fluorophenoxy)- | H | H | H | | |
| 60 | 3-((E)-CH₃O₂C.C=CH.OCH₃) | 2-(3',5'-dichloro-phenoxy)- | H | H | H | 99–102 | 7.60 |
| 61 | 3-((E)-CH₃O₂C.C=CH.OCH₃) | 2-(3'-methoxyphenoxy)- | H | H | H | 81–83 | 7.59 |
| 62 | 3-((E)-CH₃O₂C.C=CH.OCH₃) | 2-(3'-chloro-5'-methoxyphenoxy)- | H | H | H | | |
| 63 | 3-((E)-CH₃O₂C.C=CH.OCH₃) | 2-(3',4'-dichloro-phenoxy)- | H | H | H | Oil | 7.61 |
| 64 | 3-((E)-CH₃O₂C.C=CH.OCH₃) | 2-(4'-cyanophenoxy)- | H | H | H | | |
| 65 | 3-((E)-CH₃O₂C.C=CH.OCH₃) | 2-(4'-nitrophenoxy)- | H | H | H | | |
| 66 | 3-((E)-CH₃O₂C.C=CH.OCH₃) | 2-PhCH₂O— | H | H | H | 76.77 | 7.51 |
| 67 | 3-((E)-CH₃O₂C.C=CH.OCH₃) | 2-PhOCH₂— | H | H | H | Oil | 7.53 |
| 68 | 3-((E)-CH₃O₂C.C=CH.OCH₃) | 2-PhCH₂S— | H | H | H | | |
| 69 | 3-((E)-CH₃O₂C.C=CH.OCH₃) | 2-CH₃O₂C— | H | H | H | | |
| 70 | 3-((E)-CH₃O₂C.C=CH.OCH₃) | 2-C₂H₅O₂C— | H | H | H | | |
| 71 | 3-((E)-CH₃O₂C.C=CH.OCH₃) | 2-CH₂=CH.CH₂O₂C— | H | H | H | | |
| 72 | 3-((E)-CH₃O₂C.C=CH.OCH₃) | 2-PhO₂C— | H | H | H | | |
| 73 | 3-((E)-CH₃O₂C.C=CH.OCH₃) | 2-(2-methoxypyridinyl) | H | H | H | | |
| 74 | 3-((E)-CH₃O₂C.C=CH.OCH₃) | 2-(2-methoxypyridinyl) | H | H | H | | |
| 75 | 3-((E)-CH₃O₂C.C=CH.OCH₃) | 2-(5-chloro-2-methoxypyridinyl) | H | H | H | | |
| 76 | 3-((E)-CH₃O₂C.C=CH.OCH₃) | 2-(5-chloro-2-methylthiopyridinyl) | H | H | H | | |

TABLE I-continued (I)

Structure: pyridine ring with positions labeled — position 2: W, position 3: E, position 4: D, position 5: B, position 6 adjacent to N, with A on N.

| Compound No | W | A | B | D | E | Melting Point (°C.) | olefinic* |
|---|---|---|---|---|---|---|---|
| 77 | 3-((E)-CH$_3$O$_2$C.C=CH.OCH$_3$) | 2-(5-bromo-2-methoxypyridinyl) | H | H | H | | |
| 78 | 3-((E)-CH$_3$O$_2$C.C=CH.OCH$_3$) | 2-(5-bromo-2-methylthiopyridinyl) | H | H | H | | |
| 79 | 3-((E)-CH$_3$O$_2$C.C=CH.OCH$_3$) | 2-(5-trifluoromethyl-2-methoxypyridinyl) | H | H | H | | |
| 80 | 3-((E)-CH$_3$O$_2$C.C=CH.OCH$_3$) | 2-(5-trifluoromethyl-2-methylthiopyridinyl) | H | H | H | | |
| 81 | 3-((E)-CH$_3$O$_2$C.C=CH.OCH$_3$) | 2-(5-chloro-2-methoxypyrimidinyl) | H | H | H | | |
| 82 | 3-((E)-CH$_3$O$_2$C.C=CH.OCH$_3$) | 2-(5-chloro-2-methylthiopyrimidinyl) | H | H | H | | |
| 83 | 3-((E)-CH$_3$O$_2$C.C=CH.OCH$_3$) | 2-(2-methoxybenzoxazolyl) | H | H | H | | |
| 84 | 3-((E)-CH$_3$O$_2$C.C=CH.OCH$_3$) | 2-(2-methylthiobenzoxazolyl) | H | H | H | | |
| 85 | 3-((E)-CH$_3$O$_2$C.C=CH.OCH$_3$) | 2-(6-chloro-3-methoxypyrazinyl) | H | H | H | | |

TABLE I-continued

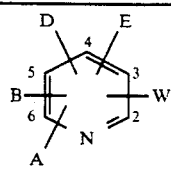

(I)

| Compound No | W | A | B | D | E | Melting Point (°C.) | olefinic* |
|---|---|---|---|---|---|---|---|
| 86 | 3-((E)-CH₃O₂C.C=CH.OCH₃) | 2- (pyrazine with Cl and SM substituents) | H | H | H | | |
| 87 | 3-((E)-CH₃O₂C.C=CH.OCH₃) | 2-(2',4'-difluorophenoxy) | H | H | H | 105-7 | 7.60 |
| 88 | 3-((E)-CH₃O₂C.C=CH.OCH₃) | 2-(3',5'-difluorophenoxy) | H | H | H | 88-89 | 7.60 |
| 89 | 3-((E)-CH₃O₂C.C=CH.OCH₃) | 2-PhO— | 6-F | H | H | | |
| 90 | 3-((E)-CH₃O₂C.C=CH.OCH₃) | 2-PhO— | 6-Cl | H | H | | |
| 91 | 3-((E)-CH₃O₂C.C=CH.OCH₃) | 2-PhO— | 4-F | 5-F | 6-F | | |
| 92 | 3-((E)-CH₃O₂C.C=CH.OCH₃) | 2-PhO— | 6-CH₃ | H | H | | |
| 93 | 3-((E)-CH₃O₂C.C=CH.OCH₃) | 2-PhO— | 4-F | 6-F | H | | |
| 94 | 3-((E)-CH₃O₂C.C=CH.OCH₃) | 2-PhO— | 6-Br | H | h | | |
| 95 | 3-((E)-CH₃O₂C.C=CH.OCH₃) | 2-PhO— | 6-CH₃O | H | H | | |
| 96 | 3-((E)-CH₃O₂C.C=CH.OCH₃) | 2-PhO— | 4-F | H | H | | |
| 97 | 3-((E)-CH₃O₂C.C=CH.OCH₃) | 2-PhO— | 5-F | H | H | | |
| 98 | 3-((E)-CH₃O₂C.C=CH.OCH₃) | 2-PhO— | 4-F | 6-CH₃ | H | | |
| 99 | 3-((E)-CH₃O₂C.C=CH.OCH₃) | 2-PhS— | 6-F | H | H | | |
| 100 | 3-((E)-CH₃O₂C.C=CH.OCH₃) | 2-CH₃ | H | H | H | Oil | 7.59 |
| 101 | 3-((E)-CH₃O₂C.C=CH.OCH₃) | 2-(2',5'-difluorophenoxy) | H | H | H | | |
| 102 | 3-((E)-CH₃O₂C.C=CH.OCH₃) | 2-(3',4'-difluorophenoxy) | H | H | H | | |
| 103 | 3-((E)-CH₃O₂C.C=CH.OCH₃) | 2-(3'-phenoxy)-phenoxy | H | H | H | | |
| 104 | 3-((E)-CH₃O₂C.C=CH.SCH₃) | 2-PhO | H | H | H | | |
| 105 | 3-((Z)-CH₃O₂C.C=CH.OCH₃) | ,2-PhO | H | H | H | | |
| 106 | 2-((E)-CH₃O₂C.C=CH.OCH₃) | H | H | H | H | Oil | 8.02 |

"Ph" means phenyl
*Chemical shift of singlet from olefinic proton on beta-methoxyacrylate group (ppm from tetramethylsilane) Solvent CDCl₃

Table II shows selected proton nmr data for certain compounds described in Table I. Chemical shifts are measured in ppm from tetramethylsilane, and deuterochloroform was used as solvent throughout. The following abbreviations are used:

TABLE II
SELECTED PROTON NMR DATA

| Compound No | Proton nmr data |
|---|---|
| 1 | 3.60(3H, s); 3.76(3H, s); 6.85-7.40(7H, m); 7.56(1H, s); 8.44(1H, t). |
| 21 | 3.55(3H, s); 3.69(3H, s); 6.94(1H, d); 7.06(2H, d); 7.45-7.60(3H, m); 7.50(1H, s); 8.0(1H, m). |
| 23 | 3.68(3H, s); 3.86(3H, s); 6.98-7.18(4H, m); 7.20-7.32(1H, m); 7.58(1H, s); 7.62-7.66 (1H, m); 8.10-8.14(1H, m). |
| 29 | 3.71(3H, s); 3.88(3H, s); 6.70(1H, d); 7.06 (2H, d); 7.23(1H, t); 7.40(2H, m); 7.64 (1H, s); 8.35(1H, d); 8.43(1H, s). |
| 43 | 3.62(3H, s); 3.80(3H, s); 6.95(2H, m); 7.08 (1H, m); 7.28(1H, m); 7.50(1H, s); 8.28 (1H, m); 8.35(1H, m). |
| 57 | 3.69(3H, s); 3.86(3H, s); 6.0-6.90(3H); 7.05(1H); 7.25-7.35(1H) 7.59(1H, s); 7.65 (1H); 8.13(1H) |
| 63 | 3.70(3H, s); 3.87(3H, s); 6.9-7.4(3H, m); 7.46(1H, d); 7.61(1H, s); 7.68(1H, q); 8.16 (1H, q). |
| 100 | 2.41(3H, s); 3.71(3H, s); 3.85(3H, s); 7.12 (1H, d); 7.59(1H, s); 8.44(1H, d). |
| 106 | 3.74(3H, s); 3.99(3H, s); 6.98(1H, m); 7.12 |

TABLE II-continued
SELECTED PROTON NMR DATA

| Compound No | Proton nmr data |
|---|---|
| | (1H, m); 7.48(1H, m); 8.02(1H, s); 8.38 (1H, m). | br = broad
s = singlet
d = doublet
J = coupling constant
t = triplet
q = quartet
m = multiplet
Hz = Hertz The compounds of the invention having the general formula (I) can be prepared by the chemical processes outlined in Scheme I, Scheme II Scheme III. Throughout Scheme I, Scheme II and Scheme III the terms R¹, R², Z, A, B, D and E are as defined above, G is hydrogen or a metal atom (such as a sodium atom), M is a metal atom (such as lithium atom) or a metal atom plus an associated halogen atom (such as MgI, MgBr, or MgCl) and L is a halogen atom or other good leaving group.

The compounds of general formula (I) may exist as mixtures of geometric isomers which can be separated by chromatography, distillation or fractional crystallisation. The use of the formula

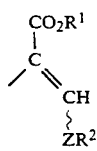

is intended to signify a separable mixture of both geometric isomers about the acrylate double bond, i.e.

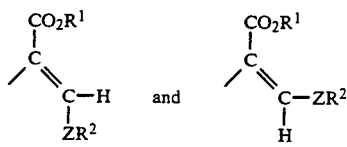

Referring to Scheme I, compounds of general formula (I), in which Z is 0 but not S, can be prepared by treatment of compounds of general formula (IV) with a base (such as sodium hydride or a sodium alkoxide) and a formic ester of the formula $HCO_2R^1$ (such as methyl formate) in a suitable solvent (step (b) of Scheme I). If a species of general formula $R^2L$, wherein L is a leaving group (such as a halide or $R^2SO_4$ anion), is then added to the reaction mixture, compounds of general formula (I) may be obtained (step (a) of Scheme I). If a protic acid is added to the reaction mixture, compounds of general formula (III) wherein G is hydrogen are obtained. Alternatively, the species of general formula (III) wherein G is a metal (usually an alkali metal such as sodium) may itself be isolated from the reaction mixture.

Compounds of general formula (III) wherein G is a metal atom can be converted into compounds of general formula (I) by treatment with a species of general formula $R^2L$, wherein L is as defined above, in a suitable solvent. Compounds of general formula (III) wherein G is hydrogen can be converted into compounds of general formula (I) by successive treatments with a base (such as potassium carbonate or sodium hydride) and a species of general formula $R^2L$, in a suitable solvent.

Alternatively, compounds of general formula (I), wherein Z is oxygen, can be prepared from acetals of general formula (XII) by elimination of the appropriate alkanol under either acidic or basic conditions, at a suitable temperature and often in a suitable solvent (step (c) of Scheme I). Examples of reagents or reagent mixtures which can be used for this transformation are lithium diisopropylamide; potassium hydrogen sulphate (see, for example, T Yamada, H Hagiwara and H Uda, *J. Chem. Soc., Chemical Communications*, 1980, 838, and references therein); and triethylamine, often in the presence of a Lewis acid such as titanium tetrachloride (see, for example, K Nsunda and L Heresi, *J. Chem. Soc., Chemical Communications*, 1985, 1000).

Acetals of general formula (XII) can be prepared by treatment of alkyl silyl ketene acetals of general formula (XIII), wherein R is an alkyl group, with a trialkyl orthoformate of formula $(R^2O)_3CH$ in the presence of a Lewis acid such as titanium tetrachloride, at a suitable temperature and in a suitable solvent (see, for example, K. Saigo, M. Osaki and T. Mukaiyama, *Chemistry Letters*, 1976, 769) (step (f) of Scheme I).

Alkyl silyl ketene acetals of general formula (XIII) can be prepared from esters of general formula (IV) by treatment with a base and a trialkylsilyl halide of general formula $R_3SiCl$ or $R_3SiBr$, such as trimethylsilyl chloride, or a base and a trialkylsilyl triflate of general formula $R_3Si-OSO_2CF_3$, in a suitable solvent and at a suitable temperature (see, for example, C. Ainsworth, F. Chen and Y Kuo, *J. Organometallic Chemistry*, 1972, 46, 59) (step (g) of Scheme I).

It is not always necessary to isolate the intermediates (XII) and (XIII); under appropriate conditions, compounds of general formula (I) may be prepared from esters of general formula (IV) in a "one pot" sequence by the successive addition of suitable reagents listed above.

Alternatively, compounds of general formula (XII), wherein Z is oxygen, can be prepared from compounds of general formula (IV) by treatment with an orthoformate $HC(ZR^2)_3$ in the presence of a carboxylic acid anhydride (such as acetic anhydride) and a Lewis acid catalyst (such as zinc chloride) at a suitable temperature. In this way, under appropriate conditions, such as elevated temperatures or extended reaction times, compounds of general formula (I) may be obtained directly (see, for example, R. Huisgen, H. Seidl and J. Wulff, *Chem. Ber*, 1969, 102, 915; and A. Marchesini, *J. Org. Chem.*, 1984, 49, 4287) (step (h) of Scheme I).

Compounds of general formula (IV) can be prepared by methods described in the chemical literature. For example, they can be prepared from compounds of general formula (V) by treatment with an alcohol $R^1OH$ in the presence of an acid (such as hydrogen chloride) (Step (d) of Scheme I).

Scheme I

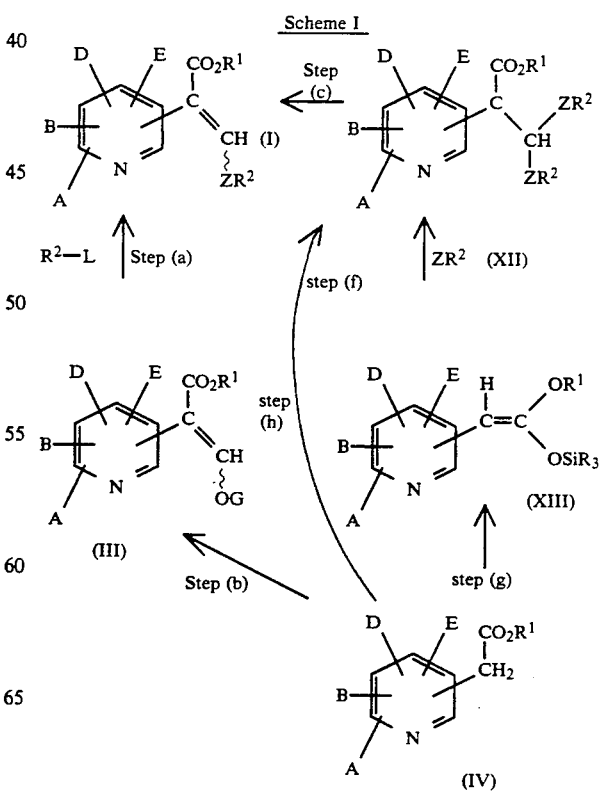

Scheme I -continued

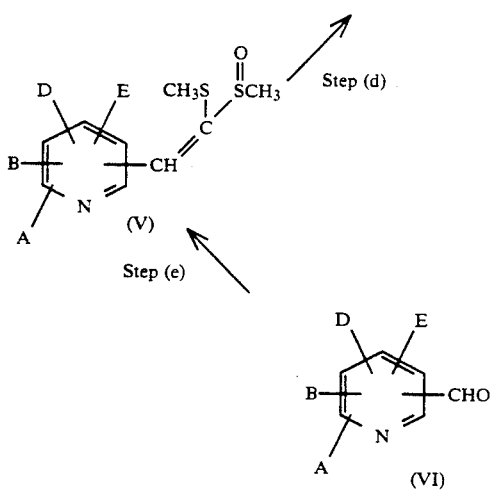

Compounds of general formula (V) can be prepared from aldehydes of general formula (VI) by treatment with methyl methylsulphinylmethylsulphide ($CH_3SOCH_2SCH_3$) in the presence of a base (such as Triton-B) in a suitable solvent (such as tetrahydrofuran) (see K. Ogura and G. Tsuchihashi, *Tetrahedron Letters*, 1972, 1383-6) (Step (e) of Scheme I).

Compounds of general formula (VI) can be prepared by standard methods described in the chemical literature.

Referring to Scheme II, compounds of general formula (I) can alternatively be prepared from alpha-ketoesters of general formula (VII) by treatment with phosphorus ylides of general formula (VIII) in a suitable solvent (such as diethyl ether or tetrahydrofuran) (see, for example, EP-A-0044448 and EP-A-0178826) (Step (a) of Scheme II).

Alpha-ketoesters of general formula (VII) can be prepared by standard methods described in the chemical literature. For example, alpha-ketoesters of general formula (VII) can be prepared by reaction of metallated pyridines of general formula (IX) with an oxalate (X) in a suitable solvent (such as diethyl ether or tetrahydrofuran) (Step (b) of Scheme II). (For related reactions, see L. M. Weinstock, R. B. Currie and A. V. Lovell, *Syn. Commun.*, 1981, 11, 943 and references therein).

Metallated pyridines of general formula (IX) can be prepared by standard methods described in the chemical literature.

Alternatively, alpha-ketoesters of general formula (VII) can be prepared from nitriles of general formula (XI) using the procedure of K. Ogura, N. Katoh, I. Yoshimura, G. Tsuchihashi, *Tetrahedron Letters*, 1978, 375 (Step (c) of Scheme II).

Scheme II

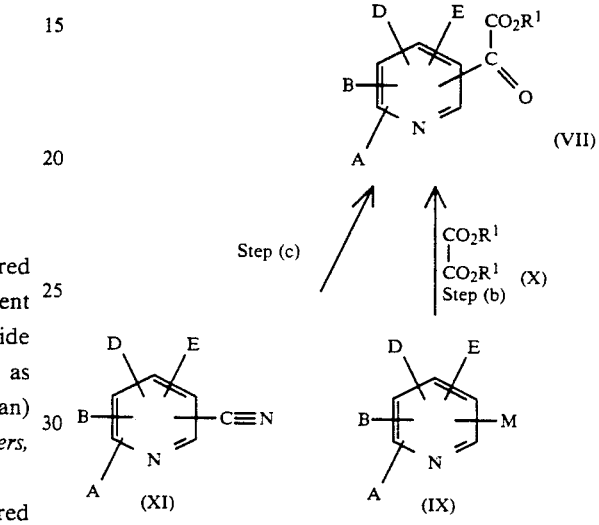

Certain of the compounds of general formula (I) can be prepared by an alternative route as shown in Scheme III.

When A is an optionally substituted phenoxymethyl, phenylthiomethyl, alkoxymethyl, alkylthiomethyl or a hydroxymethyl group, compounds of formula (I) can be prepared by reaction of a compound of general formula (XV), with an optionally substituted phenol or thiophenol in the presence of a base (such as sodium alkoxides, or sodium hydride) in a suitable solvent (such as dimethylformamide), or with an alkoxide, alkylthiolate, or hydroxide ion (step (a) of Scheme III).

Compounds of formula (XV) wherein L is a halogen can be prepared by halogenation of compounds of formula (XIV), for example by N-bromosuccinimide, in a suitable solvent such as carbon tetrachloride (step (b) of Scheme III).

Compounds of general formula (XIV) can be prepared by the route shown in Scheme I.

Compounds of general formula (I), where A is an optionally substituted alkenyl or optionally substituted phenylalkenyl group of the formula $-CHR^5=CR^6R^7$ can be prepared by reaction of compounds of general formula (XVI) with compounds of general formula (XVII), under the conditions of the well known Wadsworth-Emmons reaction (where Y is the group $-P(O)(OR^8)_2$) or under the conditions of the well known Wittig reaction (where Y is $-{}^+PAr_3$ and Ar is an optionally substituted phenyl group). Thus, compounds of general formula (XVI) are treated with a suitable base (such as sodium hydride or potassium t-butoxide) in a suitable dry solvent (such as N,N-dimethylformamide or tetrahydrofuran) and then treated with the compounds of general formula (XVII) (step (c) of Scheme III).

Compounds of general formula (XVI) can be prepared by reaction of compounds of general formula (XV) with a trialkyl phosphite, $P(OR^8)_3$, or with a triarylphosphine in a suitable solvent such as toluene or diethyl ether (step (d) of Scheme III).

Throughout Scheme III $R^5$ is preferably hydrogen, but may also be $C_{1-4}$ alkyl, or optionally substituted phenyl; $R^6$ and $R^7$ are hydrogen, $C_{1-8}$ alkyl, haloalkyl, optionally substituted phenyl or the group $-CO_2R^3$. Preferably one of $R^6$ and $R^7$ is hydrogen and $R^8$ is $C_{1-4}$ alkyl, usually methyl or ethyl. L is as defined for Scheme I, but is preferably a halogen atom such as chlorine or bromine.

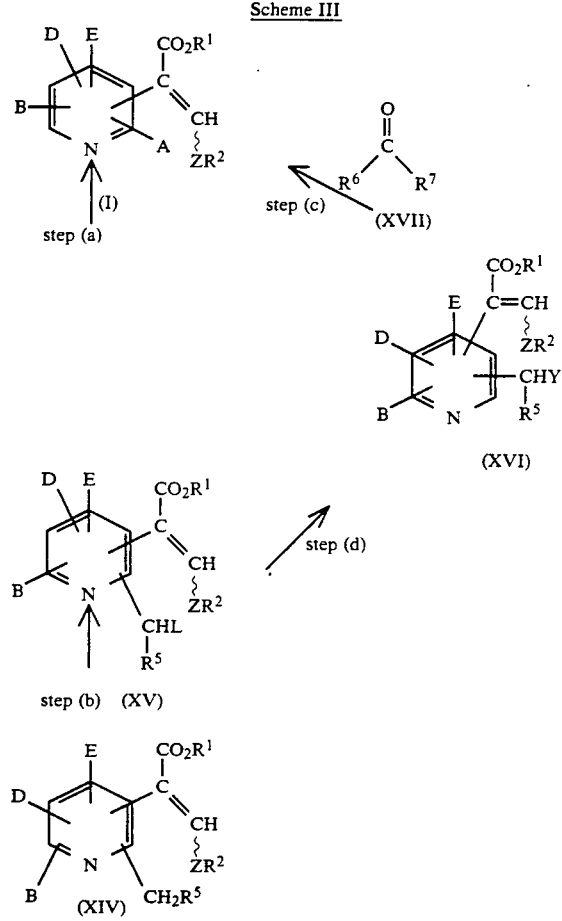

Scheme III

In further aspects, the invention provides processes as herein described for preparing the compounds of the invention and the intermediate chemicals of formulae (III), (IV), (V), (VII), and (XII)-(XVI) used therein.

The compounds and metal complexes of the invention are active fungicides, and may be used to control one or more of the pathogens:

*Pyricularia oryzae* on rice

*Puccinia recondita, Puccinia striiformis* and other rusts on wheat, *Puccinia hordei, Puccinia striiformis* and other rusts on barley, and rusts on other hosts e.g., coffee, pears, apples, peanuts, vegetables and ornamental plants. *Erysiphe graminis* (powdery mildew) on barley and wheat and other powdery mildews on various hosts such as *Sphaerotheca macularis* on hops

*Sphaerotheca fuliginea* on cucurbits (e.g., cucumber), *Podosphaera leucotricha* on apples and *Uncinula necator* on vines.

Helminthosporium spp., Rhynchosporium spp., Septoria spp. and *Pseudocercosporella herpotrichoides* on cereals. *Cercospora arachidicola* and *Cercosporidium personata* on peanuts and other Cercospora species on other hosts for example sugar beet, bananas, soya beans and rice.

Alternaria species on vegetables (e.g., cucumber), oil seed rape, apples, tomatoes and other hosts.

*Venturia inaequalis* (scab) on apples

*Plasmopara viticola* on vines

Other downy mildews such as *Bremia lactucae* on lettuce, Peronospora spp. on soybeans, tobacco, onions and other hosts and *Pseudoperonospora humuli* on hops and *Pseudoperonospora cubensis* on cucurbits

*Phytophthora infestans* on potatoes and tomatoes and other Phytophthora spp. on vegetables, strawberries, avocado, pepper, ornamentals, tobacco, cocoa and other hosts.

Some of the compounds have shown a broad range of activities against fungi in vitro.

Some of the compounds may also have activity against various post-harvest diseases of fruit (e.g., *Penicillium digitatum* and *italicum* and *Trichoderma viride* on oranges and *Gloesporium musarum* on bananas).

Further some of the compounds may be active as seed dressings against Fusarium spp., Septoria spp., Tilletia spp. (bunt, a seed borne disease of wheat), Ustilago spp., Helminthosporium spp. on cereals, and *Pyricularia oryzae* on rice.

Therefore, in another aspect of the invention there is provided a method of combating fungi, which comprises applying to a plant, to a seed of a plant, or to the locus of the plant or seed, an effective amount of a fungicidal compounds of formula (I).

Some of the compounds can move acropetally in the plant tissue. Moreover, the compounds may be volatile enough to be active in the vapour phase against fungi on the plant.

The compounds may also be useful as industrial (as opposed to agricultural) fungicides, e.g., in the prevention of fungal attack on wood, hides, leather and especially paint films.

The compounds of the invention have useful insecticidal activity against a range of insect species, and nematodes. Therefore in a further aspect of the invention there is provided a method of killing or controlling insect or nematode pests which comprises administering to the insect or nematode or to a locus thereof an effective amount of an insecticidal compound of formula (I).

A preferred group of compounds for use in this aspect of the invention are compounds of formula (I) where A is optionally substituted aryloxy (in particular at the 2-position) B, D and E are hydrogen and W is at the 3-position in the ring.

Particularly preferred compounds for use in this aspect of the invention are compound 15 in Table I, which has been found to be active against *Meloidogyne incognita* (tomato root-knot eelworm larvae) and compound 23 in Table I which has been found to be active against *Diabrotica balteata* (root worm larvae).

Similarly, some compounds may exhibit plant growth regulating activity and may be deployed for this purpose at appropriate rates of application. Therefore in yet a further aspect of the invention there is provided a method of regulating plant or seed, or to a locus thereof, growth which comprises applying to a plant an effective amount of a plant growth regulating compound of formula (I).

The compounds may be used directly for fungicidal, insecticidal, nematocidal or plant growth regulating purposes but are more conveniently formulated into compositions using a carrier or diluent. The invention thus provides a fungicidal composition comprising a compound of general formula (I) as hereinbefore defined, and a fungicidally acceptable carrier or diluent.

In addition the invention provides an insecticidal/nematocidal composition which comprises an insecticidal or nematocidal compound of formula (I) in combination with a carrier or diluent and a plant growth regulating composition which comprises a plant growth regulating compound of formula (I) with a carrier or diluent.

As fungicides, the compounds can be applied in a number of ways. For example they can be applied, formulated or unformulated, directly to the foliage of a plant, to seeds or to the medium in which plants are growing or are to be planted. They can be sprayed on, dusted on or applied as a cream or paste formulation; or they can be applied as a vapour or as slow release granules. Application can be to any part of the plant including the foliage, stems, branches or roots, or to soil surrounding the roots, or to the seed before it is planted; or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example fillers such as kaolin, bentonite, kieselguhr, dolomite, calcium carbonate, talc, powdered magnesia, Fuller's earth, gypsum, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example a mineral oil) for assisting the adhesion of the composition to the seed; alternatively the active ingredient can be formulated for seed dressing purposes using an organic solvent (for example N-methylpyrrolidone, propylene glycol or dimethylformamide). The compositions may also be in the form of wettable powders or water dispersible granules comprising wetting or dispersing agents to facilitate their dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as isophorone, cyclohexanone and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent and including a suspending agent to stop the solid settling.

Compositions to be used as sprays may be in the form of aerosols wherein the formulation is held in a container under pressure in the presence of a propellant, eg, fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in a microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (eg, nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants eg, a wetting agent, dispersing agent, emulsifying agent or suspending agent. These agents can be cationic, anionic or non-ionic agents.

Suitable cationic agents are quaternary ammonium compounds, for example cetyltrimethylammonium bromide. Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, eg, compounds having similar or complementary fungicidal activity or which possess plant growth regulating, herbicidal or insecticidal activity.

A fungicidal compound which may be present in the composition of the invention may be one which is capable of combating ear diseases of cereals (eg, wheat) such as Septoria, Gibberella and Helminthosporium spp., seed and soil borne diseases and downy and powdery mildews on grapes and powdery mildew and scab on apple etc. By including another fungicide the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are carbendazim, benomyl, thiophanate-methyl, thiabendazole, fuberidazole, etridazole, dichlofluanid, cymoxanil, oxadixyl, ofurace, metalaxyl, furalaxyl, 4-chloro-N-(1-cyano-1-ethoxymethyl)benzamide, benalaxyl, fosetyl-aluminium, fenarimol, iprodione, prothiocarb, procymidone, vinclozolin, penconazole, myclobutanil, propamocarb, diniconazole, pyrazophos, ethirimol, ditalimfos, tridemorph, triforine, nuarimol, triazbutyl, guazatine, triacetate salt of 1,1'-iminodi(octamethylene)diguanidine, buthiobate, propiconazole, prochloraz, flutriafol, hexaconazole, (2RS,3RS)-2-(4-chlorophenyl)-3-cyclopropyl-1-(1H-1,2,4-triazol-1-yl)butan-2-ol, (RS)-1-(4-chlorophenyl)-4,4-dimethyl-3-(1H-1,2,4-triazol-1-ylmethyl)pentan-3-ol, flusilazole, triadimefon, triadimenol, diclobutrazol, fenpropimorph, pyrifenox, fenpropidin, chlorozolinate, imazalil, fenfuram, carboxin, oxycarboxin, methfuroxam, dodemorph, BAS 454, blasticidin S, kasugamycin, edifenphos, Kitazin P, cycloheximide, phthalide, probenazole, isoprothiolane, tricyclazole, pyroquilon, chlorbenzthiazone, neoasozin, polyoxin D, validamycin A, mepronil, flutolanil, pencycuron, diclomezine, phenazin oxide, nickel dimethyldithiocarbamate, techlofthalam, bitertanol, bupirimate, etaconazole, hydroxyisoxazole, streptomycin, cypofuram, biloxazol, quinomethionate, dimethirimol, 1-(2-cyano-2-methoxyiminoacetyl)-3-ethyl urea, fenapanil, tolclofos-methyl, pyroxyfur, polyram, maneb, mancozeb, captafol, chlorothalonil, anilazine, thiram, captan, folpet, zineb, propineb, sulphur, dinocap, dichlone, chloroneb, binapacryl, nitrothal-isopropyl, dodine, dithianon, fentin hydroxide, fentin acetate, tecnazene, quintozene, dicloran, copper containing compounds such as copper oxychloride, copper sulphate and Bordeaux mixture, and organomercury compounds.

The compounds of general formula (I) can be mixed with soil, peat or other rooting media for the protection of plants against seed-borne, soil-borne or foliar fungal diseases.

Suitable insecticides which may be incorporated in the composition of the invention include pirimicarb, dimethoate, demeton-s-methyl, formothion, carbaryl, isoprocarb, XMC, BPMC, carbofuran, carbosulfan, diazinon, fenthion, fenitrothion, phenthoate, chlorpyrifos, isoxathion, propaphos, monocrotophas, buprofezin, ethroproxyfen and cycloprothrin.

Plant growth regulating compounds are compounds which control weeds or seedhead formation, or selectively control the growth of less desirable plants (e.g., grasses).

Examples of suitable plant growth regulating compounds for use with the invention compounds are the gibberellins (e.g., $GA_3$, $GA_4$ or $GA_7$), the auxins (e.g., indoleacetic acid, indolebutyric acid, naphthoxyacetic acid or naphthylacetic acid), the cytokinins (e.g., kinetin, diphenylurea, benzimidazole, benzyladenine or benzylaminopurine), phenoxyacetic acids (e.g., 2,4-D or MCPA), substituted benzoic acids (e.g., triiodobenzoic acid), morphactins (e.g., chlorfluoroecol), maleic hydrazide, glyphosate, glyphosine, long chain fatty alcohols and acids, dikegulac, paclobutrazol, flurprimidol, fluoridamid, mefluidide, substituted quaternary ammonium and phosphonium compounds (e.g., chloromequat chlorphonium or mepiquatchloride), ethephon, carbetamide, methyl-3,6-dichloroanisate, daminozide, asulam, abscisic acid, isopyrimol, 1-(4-chlorophenyl)-4,6-dimethyl-2-oxo-1,2-dihydropyridine-3-carboxylic acid, hydroxybenzonitriles (e.g., bromoxynil), difenzoquat, benzoylprop-ethyl 3,6-dichloropicolinic acid, fenpentezol, inabenfide, triapenthenol and tecnazene.

The following Examples illustrates the invention. Throughout these examples, the term "ether" refers to diethyl ether, magnesium sulphate was used to dry solutions, and reactions involving water-sensitive intermediates were performed under nitrogen and in dried solvents. Unless otherwise stated, chromatography was performed using silica gel as the stationary phase. Where shown, infrared and NMR data are selective; no attempt is made to list every absorption. The following abbreviations are used throughout:

| THF = tetrahydrofuran | delta = chemical shift |
|---|---|
| DMF = N,N-dimethylformamide | $CDCl_3$ = deuterochloroform |
| | s = singlet |
| | d = doublet |
| GC = Gas chromatography | t = triplet |
| MS = Mass spectrum | m = multiplet |
| mmHg = millimetres pressure of mercury | J = coupling constant |
| | Hz = Hertz |
| mg = milligramme(s) | NMR = clear Magnetic Resonance |
| g = gramme(s) | |

EXAMPLE 1

This Example illustrates the preparation of (E)-methyl 2-(2'-phenoxypyrid-3'-yl)-3-methoxyacrylate (Compound No 15 of Table I).

2-Phenoxy-3-cyanopyridine (20 g) and Raney-nickel alloy (20 g) were stirred at reflux in 75% formic acid (200 ml) for 1 hour. The reaction mixture was cooled and filtered and the resultant green solution was poured into water (150 ml). After standing for several hours, needles of 2-phenoxy-3-pyridinecarboxaldehyde were deposited which were collected by filtration, washed with water and air-dried (10 g); m.p. 88°–90° C.; infrared max (nujol) 1675 cm$^{-1}$; $^1$H NMR delta ($CDCl_3$) 7.0–7.6 (m), 8.15–8.4 (2H,m), 11.05 (1H,s).

To a stirred solution of 2-phenoxy-3-pyridinecarboxaldehyde (9.95 g, 0.05 mol) and methyl methylsulphinylmethyl sulphide (6.2 g, 0.05 mol) in dry THF (20 ml) was added dropwise Triton B (7.5 ml, 40% solution in methanol). The reaction mixture was then heated to reflux for 1 hour. GC analysis indicated that the reaction had gone to completion. The reaction mixture was allowed to cool and the solvent removed under reduced pressure. The brown oily residue was extracted repeatedly with ether and the combined ether extracts evaporated to give a white crystalline solid which was washed with a little ether and air-dried (7 g); m.p. 123°-6° C.; infrared max (nujol) 1565, 1400, 1235, 1200, 1060 cm$^{-1}$; $^1$H NMR delta (CDCl$_3$) 2.33 (3H,s), 2.8 (3H,s), 6.87-7.7 (m), 8.07 (1H,s), 8.1-8.6 (m). The product (6.8 g) was dissolved in methanolic hydrogen chloride (150 ml) (formed by adding acetyl chloride to methanol (1:5) at 0° C.) stirred for 1 hour at 0° C. and then left overnight. The reaction mixture was poured into water, neutralised with bicarbonate solution and then extracted with ether. The combined ether extracts were dried, filtered and evaporated to give a pale yellow liquid. Bulb-to-bulb distillation (150° C./0.1 mmHg) afforded methyl 2-phenoxypyrid-3-yl acetate (4.5 g) infrared max (film) 1735, 1580, 1485, 1430, 1245 cm$^{-1}$; $^1$H NMR delta (CDCl$_3$) 3.71 (3H,s), 3.80 (2H,s), 6.90-8.2 (m).

To a stirred solution of petrol-washed sodium hydride (1.8 g, 0.037 mol), 48% dispersion in oil) in dry DMF (30 ml) at −15° C. was added drop-wise a solution of methyl 2-phenoxypyrid-3-yl acetate (4.5 g, 0.0185 mol) and methyl formate (24 g, 0.4 mol) in dry DMF (20 ml). A yellow colour formed, accompanied by effervescene. After 30 minutes, the temperature was allowed to rise slowly. After stirring at room temperature for 30 minutes, the reaction mixture was poured into water (250 ml) and extracted twice with ether. The combined ether extracts were then washed with potassium carbonate solution. The aqueous layers were combined, acidified to pH 4 with conc. hydrochloric acid and then thoroughly re-extracted with ether. The resultant ether extracts were dried, filtered and evaporated to give an oil (5.4 g). The oil (5.4 g) and potassium carbonate (2.55 g) were added to dry DMF (20 ml) at 0° C. Dimethylsulphate (1.75 ml) was added in one portion and the temperature allowed to rise to room temperature. GC analysis indicated that the reaction had gone to completion. The reaction mixture was poured into water (150 ml) and ether (10 ml) added. White crystals were deposited which were collected by filtration. Recrystallisation from ethyl acetate/60°-80° C. petroleum ether gave (E)-methyl 2-(2'-phenoxypyrid-3'-yl)-3-methoxyacrylate (3.4 g); m.p. 121°-123° C.; infrared max (nujol) inter alia 1710, 1635, 1575 cm$^{-1}$; $^1$H NMR delta (CDCl$_3$) 3.7 (3H,s), 3.85 (3H,s), 6.9-7.45 (m), 7.60 (1H,s), 7.5-7.75 (m), 8.1 (m) ppm.

EXAMPLE 2

This Example illustrates the preparation of (E)-methyl-2-(3'-phenoxypyrid-4'-yl)-3-methoxyacrylate (Compound No 43 of Table I).

To a solution of 3-phenoxypyridine (10.26 g, 0.06 mol) in dry THF (500 ml) under nitrogen was added copper(I) iodide and methyl sulphide (30 ml). The mixture was stirred at room temperature for 15 minutes and then cooled to −25° C. Phenyl chloroformate (8.0 ml, 0.066 mol) was then added dropwise to produce a dark-brown solution. After 10 minutes methylmagnesium bromide (20 mls of 3M solution, 0.066 mol) was added dropwise at −25° C. After stirring at −25° C. for 15 minutes the solution was warmed to room temperature over 1 hour, during which time the solution had become a clear light yellow colour. The reaction was quenched with 20% aqueous ammonium chloride solution (150 ml) and then partitioned with ether (250 ml). The organic layer was washed with 20 ml portions of 20% aqueous ammonium chloride-ammonium hydroxide (1:1) solution, 10% hydrochloric acid, water and brine. After drying the ether was evaporated to give a yellow oil which was redissolved in dry toluene (250 ml). A suspension of o-chloranil (15 g) in toluene (100 ml) was added portionwise at room temperature. The resulting dark solution was stirred overnight and then 10% aqueous sodium hydroxide solution (200 ml) was added and stirring continued for 10 minutes at room temperature. The reaction mixture was partitioned with ether (200 ml) and the organic layer washed with 200 ml portions of 10% aqueous sodium hydroxide solution and water and then 10% hydrochloric acid (4×250 ml). The acidic extracts were basified with 25% aqueous sodium hydroxide solution and then extracted with methylene chloride (×4). The combined methylene chloride extracts were dried and evaporated to give a yellow oil. Bulb-to-bulb distillation (100° C. at 0.05 mBar) afforded 3-phenoxy-4-methylpyridine (6.5 g) as a clear liquid, $^1$H NMR delta (CDCl$_3$) 2.25 (3H,s); 6.9-7.4 (6H,m); 8.2 (1H,s); 8.3 (1H,d).

n-Butyllithium (6.1 ml of 2.6M solution in hexane, 0.0157 mol) was added dropwise to a stirred solution of 3-phenoxy-4-methylpyridine (2.9 g, 0.0157 mol) in dry THF (20 ml) at −78° C. under an atmosphere of nitrogen. The resulting brown suspension was stirred for 30 minutes and then a steady stream of carbon dioxide was bubbled through. After 30 minutes, the reaction mixture was poured into water (100 ml) and extracted (×2) with ether. The aqueous layer was evaporated to dryness under vacuum at 60° C. The resulting white solid was then treated with 150 ml of methanol saturated with hydrogen chloride and the resulting yellow solution left overnight. The solvent was removed under reduced pressure and the residue partitioned between methylene chloride (100 ml) and saturated aqueous bicarbonate solution (100 ml). The organic layer was separated and the aqueous layer re-extracted (×2) with more methylene chloride. The combined organic extracts were dried and evaporated to give a brown liquid (2.5 g). Bulb-to-bulb distillation (140° C. at 0.1 mBar) afforded methyl 3-phenoxypyrid-4-yl acetate (2.15 g) as a pale yellow liquid; infrared maximum 1735 cm$^{-1}$, $^1$H NMR delta (CDCl$_3$) inter alia 3.60 (3H,s); 3.72 (2H,s).

Trimethylsilyltriflate (2.22 g, 0.01 mol) was added dropwise to a solution of triethylamine (1.01 g, 0.01 mol) in ether (10 ml) at room temperature. The resulting clear solution was added dropwise to a stirred solution of methyl 3-phenoxypyrid-4-yl acetate (2.0 g, 0.00823 mol) in ether (10 ml) at 0° C. The two-phase mixture was stirred for 1 hour at room temperature and then stood overnight at room temperature under nitrogen. The resulting brown oil was diluted with methylene chloride (5 ml) and transferred to a dropping funnel. In a separate flask, titanium tetrachloride (1.9 g, 0.01 mol) was dissolved in methylene chloride (10 ml) and then added dropwise to a solution of trimethyl orthoformate (1.1 g, 0.01 mol) in methylene chloride (15 ml) at −70° C. The resulting yellow suspension was stirred at −70° C. whilst the preformed solution of the silyl enol ether was added dropwise. The internal temperature rose to −50° C. The reaction mixture was stirred rapidly, allowed to rise slowly to room temperature and then stood overnight. The resulting reaction mixture was poured into 5% potassium carbonate solution (200 ml) and then extracted with ether (×3). The dried ether extracts were evaporated to give a brown oil. Chromatography on silica (eluent ether) afforded the title compound (0.89 g) as a clear liquid; infrared maxima 1700, 1630 cm$^{-1}$; $^1$H NMR delta (CDCl$_3$) 3.62 (3H,s); 3.80 (3H,s); 6.95 (2H,m); 7.08 (1H,m); 7.28 (3H,m); 7.50 (1H,s); 8.28 (1H,m); 8.35 (1H,m).

EXAMPLE 3

This example illustrates the preparation of (E)-methyl 2-(4'-phenoxypyrid-3'-yl)-3-methoxyacrylate (Compound No 29 of Table I).

A solution of 4-chloropyridine (2.89 g, 25.5 mmol) in THF (15 ml) at −78° C. was added to a stirred solution of lithium di-isopropylamide prepared by addition of n-butyl lithium (10.2 ml of 2.5M, 25.5 mmol) to a solution of diisopropylamine (2.58 g, 25.5 mmol) in dry tetrahydrofuran at −78° C. After 2 hours a solution of DMF (2.05 g, 28.1 mmol) in THF (25 ml) at −78° C. was added. After a further 1 hour at −78° C. the reaction mixture was allowed to warm slowly to room temperature (16 hours). The resulting solution was poured into saturated brine (200 ml) and extracted with ether (3×100 ml). The combined ether extracts were washed with saturated brine and then the solvent was evaporated. Flash chromatography (eluent petrol-ether) of the resulting residue gave 4-chloro-3-pyridine carboxaldehyde (2.86 g) as a solid; melting point 53°-54° C.; infrared max (nujol) 1580, 1695 cm$^{-1}$; $^1$H NMR delta (CDCl$_3$) 7.45 (1H,d), 8.70 (1H,d), 9.07 (1H,s), 10.50 (1H,s).

A solution of phenol (1.34 g, 14.3 mmol) in DMF (25 ml) was stirred with anhydrous potassium carbonate (0.99 g, 7.2 mmol) at 70°-80° C. for 40 minutes. 4-Chloro-3-pyridinecarboxaldehyde (2.02 g, 14.3 mmol) and copper bronze powder (0.10 g) were added and the resulting suspension stirred at 100°-110° C. for 2 hours. The reaction mixture was cooled, filtered and the residues washed with ether. The combined ether washings were diluted to 400 ml with more ether, washed with saturated brine (4×) and the solvent removed to give 4-phenoxy-3-pyridinecarboxaldehyde as a pale yellow crystalline solid (2.62 g); melting point 74°-75° C.; infrared max (nujol) 1590, 1695, 2760 cm$^{-1}$; $^1$H NMR delta (CDCl$_3$) 6.75 (1H broad), 7.15 (2H,d), 7.35 (1H,t), 7.50 (2H,t), 8.5-9.7 (2H,broad), 10.7 (1H,s).

To a stirred solution of 4-phenoxy-3-pyridinecarboxaldehyde (0.687 g, 3.45 mmol) and methyl methylsulphinylmethyl sulphide (0.429 g, 3.45 mmol) in THF was added dropwise Triton B (0.53 ml, 40% solution in methanol). The mixture was heated at reflux for 2 hours, allowed to cool and then diluted with dichloromethane (150 ml). The solution was washed with saturated brine (2×) and the solvent was evaporated. Flash chromatography (eluent ether-ethyl acetate) of the resulting residue gave 3-(2'-methylsulphinyl-2'-methylthiovinyl)-4-phenoxypyridine as a pale yellow gum (0.128 g); $^1$H NMR delta (CDCl$_3$) 2.32 (3H,s), 2.77 (3H,s), 6.60 (1H,d), 6.9-7.5 (5H,m), 7.93 (1H,s), 8.32 (1H,d), 9.10 (1H,s).

3-(2'-Methylsulphinyl-2'-methylthiovinyl)-4-phenoxypyridine (0.128 g, 0.42 mmol) was dissolved in methanolic hydrogen chloride [formed by adding acetyl chloride (1.2 ml) to dry methanol (12 ml)], and the solution was stirred overnight at ambient temperature. The reaction mixture was evaporated to dryness, stirred with aqueous sodium bicarbonate solution (25 ml) and then extracted with dichloromethane (2×). The combined extracts were washed with saturated brine and the solvent was evaporated. Flash chromatography (eluent ether) gave methyl (4'-phenoxypyrid-3'-yl)acetate as a pale brown oil (0.066 g); infrared max (film) 1580, 1740 cm$^{-1}$; $^1$H NMR delta (CDCl$_3$) 3.68 (3H,s), 3.74 (2H,s), 6.58 (1H,d), 7.0-7.5 (5H,m), 8.3-8.6 (2H,m).

To a stirred suspension of petrol-washed sodium hydride (0.026 g, 0.54 mmol, 50% dispersion in oil) in DMF (4 ml) was added a solution of methyl (4'-phenoxypyrid-3'-yl)acetate (0.066 g, 0.27 mmol) and methyl formate (0.39 g, 6.5 mmol) in DMF. The mixture was stirred for 3.5 hours at ambient temperature. To the resulting almost clear pale yellow brown solution was added dropwise a solution of dimethyl sulphate (0.068 g, 0.54 mmol) in DMF (1.5 ml) and stirring continued for a further 2.5 hours at ambient temperature. The reaction mixture was then poured into saturated brine (50 ml) and extracted with ether (2x). The combined ether extracts were washed with saturated brine and then the solvent removed. Flash chromatography (eluent ether) of the resulting residue afforded (E)-methyl 2-(4'-phenoxypyrid-3'-yl)-3-methoxyacrylate as a pale yellow gum (0.032 g); $^1$H NMR (CDCl$_3$) as in Table II.

EXAMPLE 4

This example illustrates the preparation of (E)-methyl 2-(3'-phenoxypyrid-2'-yl)-3-methoxyacrylate (compound No 1 of Table 1).

To a stirred solution of 2-methyl-3-hydroxypyridine (20 g, 0.1834 mol) in DMF (40 ml) was added sodium hydroxide (7.4 g), copper bronze (1 g) and bromobenzene (38.7 ml, 0.367 mol). The reaction mixture was heated to 153° C. overnight. During this time, 40 ml of a volatile component distilled out of the reaction mixture, which was replaced with more bromobenzene. The reaction mixture was partitioned between ether and water, and the ether layer washed with water, dried and evaporated to give a brown oil (13 g). Bulb-to-bulb distillation (0.5 mmHg, 150° C.) gave 2-methyl-3-phenoxypyridine as a colourless oil (5 g) contaminated with traces of DMF ($^1$H NMR evidence). The oil was redissolved in ether, washed with water, dried and evaporated to give 2-methyl-3-phenoxypyridine (3.6 g) as a clear colourless oil; $^1$H NMR delta (CDCl$_3$) 2.52 (3H,s); 6.84-7.44 (7H,m); 8.78 (1H,m).

To a stirred solution of 2-methyl-3-phenoxypyridine (3.2 g, 0.017 mol) in THF (25 ml) at −60° C. was added n-butyllithium (7 ml of a 2.5M solution in hexane) via syringe over 15 minutes. A deep red colour formed immediately and there was a slight exotherm. After stirring for a further 20 minutes, carbon dioxide gas was passed over the reaction mixture. A mildly exothermic reaction took place and a cream precipitate formed. The reaction mixture was allowed to warm to room temperature over 2 hours, diluted with water (100 ml), and then extracted with dichloromethane (×2) and ether (×1). The aqueous phase was evaporated in vacuo at 50° C., and the resulting cream-coloured residue redissolved in methanolic hydrogen chloride [formed from acetyl chloride (10 ml) and methanol (100 ml)] and left overnight at room temperature. The solvent was removed in vacuo and the residue redissolved in dichloromethane and washed with dilute sodium hydrogen carbonate. The organic phase was dried and evaporated to give an oily residue. Chromatography (eluent dichloromethane-ether) afforded methyl (3-phenoxypyrid-2-yl)acetate (1.5 g) as a brown oil; infrared max (film)1735, 1400, 1250 cm$^{-1}$.

Methyl (3-phenoxypyrid-2-yl)acetate (1.0 g) was dissolved in a mixture of trimethylorthoformate (25 ml) and acetic anhydride and a catalytic amount of anhydrous zinc chloride added. The resulting reaction mixture was stirred at reflux for 3 hours. GC analysis of an aliquot indicated the loss of the starting material with the formation of two new products. The dark brown reaction mixture was cooled and evaporated to dryness in vacuo. The residue was partitioned between ether and dilute aqueous sodium hydrogen carbonate solution. The ether layer was dried and evaporated to give a brown oily residue (1.26 g). Chromatography (eluent ether-dichloromethane, 1:1) afforded both methyl 3,3-dimethoxy-2-(3'-phenoxypyrid-2'-yl)propanoate as a yellow oil (730 mg); infrared max (film) 1735, 1440, 1245, 1070, 750 cm$^{-1}$; $^1$H NMR delta (CDCl$_3$) 3.24 (3H,s); 3.45 (3H,s); 3.60 (3H,s); 4.65 (1H,d); 5.38 (1H,d); and (E)-methyl 2-(3'-phenoxypyrid-2'-yl)-3-methoxyacrylate as a yellow oil (210 mg); infrared max (film) 1710, 1635, 1435, 1260, 1130 cm$^{-1}$; $^1$H NMR delta (CDCl$_3$) 3.60 (3H,s); 3.76 (3H,s); 6.85–7.40 (7H,m); 7.56 (1H,s); 8.44 (1H,t); m/e 285 (M+), 270, 254, 226.

EXAMPLE 5

This example illustrates the preparation of (E)-methyl 2-(2'-phenoxymethylpyridin-3'-yl)-3-methoxyacrylate (Compound No 67 of Table 1).

To a stirred suspension of sodium hydride (0.62 g, 60% dispersion in oil) in DMF (15 ml) at 0° C. was added dropwise a solution of methyl (2-methylpyridin-3-yl)acetate (1.968 g) and methyl formate (3.6 g) in DMF (5 ml). The solution was stirred at room temperature for 30 minutes and then allowed to stand overnight. The reaction mixture was poured into water (250 ml) and extracted with ether (100 ml). The aqueous layer was adjusted to pH 7 with dilute hydrochloric acid and then extracted with ethyl acetate (3×100 ml). The organic extracts were combined, dried and then evaporated under reduced pressure to give methyl 2-(2'-methylpyridin-3'-yl)-3-hydroxyacrylate as a brown oil (2.83 g, containing 58% DMF by NMR). The crude oil (2.83 g) was stirred in DMF (40 ml) with dimethyl sulphate (1.59 g) and potassium carbonate (3.31 g) at room temperature for 30 minutes, then allowed to stand overnight. The reaction mixture was poured into water (300 ml), the solution adjusted to pH 8 with dilute hydrochloric acid and then extracted with ethyl acetate (3×200 ml). The combined organic layers were washed with water (3×50 ml), then dried and evaporated under reduced pressure to give (E)-methyl 2-(2'-methylpyridin-3'-yl)-3-methoxyacrylate as a yellow liquid (0.72 g). Infrared max 1717, 1640, 1260 cm$^{-1}$; $^1$H NMR delta (CDCl$_3$) 2.41 (3H,s), 3.71 (3H,s), 3.85 (3H,s), 7.12 (1H,m), 7.41 (1H,d), 7.59 (1H,s), 8.44 (1H,d) ppm.

(E)-methyl 2-(2'-methylpyridin-3'-yl)-3-methoxyacrylate (0.72 g) was stirred in carbon tetrachloride (25 ml) with N-bromosuccinimide (0.84 g) and azoisobutyronitrile (0.025 g, catalyst) and then heated to reflux for 3.5 hours. The reaction mixture was partitioned between saturated sodium bicarbonate solution (100 ml) and ethyl acetate (120 ml). The aqueous layer was further extracted with ethyl acetate (2×30 ml). The combined organic layers were washed with water (20 ml), and then dried and evaporated under reduced pressure to give (E)-methyl 2-(2'-bromomethylpyridin-3'-yl)-3-methoxyacrylate as a brown oil (1.14 g), which was used without further purification. The oil in DMF (5 ml) was added to a stirred solution of sodium phenoxide (0.41 g) in DMF (5 ml), then stirred at room temperature for 30 minutes and allowed to stand for 64 hours. The reaction mixture was poured into water (200 ml) and extracted with ethyl acetate (3×100 ml). The combined organic extracts were washed with water, (2×30 ml), dried and evaporated under reduced pressure to give a brown oil (0.97 g) which was purified by HPLC (eluent ethyl acetate) to give (E)-methyl 2-(2'-phenoxymethylpyridin-3'-yl)-3-methoxyacrylate as a light brown oil, (0.194 g), infrared max (film) 1715, 1640, 1260, 1135 cm$^{-1}$; $^1$H NMR delta (CDCl$_3$) 3.66 (3H,s), 3.76 (3H,s), 5.12 (2H,s), 6.82–6.98 (3H,m), 7.16–7.32 (3H,m), 7.51 (1H,d), 7.53 (1H,s), 8.6 (1H,d) ppm.

The following are examples of compositions suitable for agricultural and horticultural purposes which can be formulated from the compounds of the invention. Percentages are by weight.

EXAMPLE 6

An emulsifiable concentrate is made up by mixing and stirring the ingredients until all are dissolved.

| Compound No 15 | 10% |
| Benzyl alcohol | 30% |
| Calcium dodecylbenzenesulphonate | 5% |
| Nonylphenolethoxylate (13 moles ethylene oxide) | 10% |
| Alkyl benzenes | 45% |

EXAMPLE 7

The active ingredient is dissolved in methylene dichloride and the resultant liquid sprayed onto the granules of attapulgite clay. The solvent is then allowed to evaporate to produce a granular composition.

| Compound No 15 | 5% |
| Attapulgite granules | 95% |

EXAMPLE 8

A composition suitable for use as a seed dressing is prepared by grinding and mixing the three ingredients.

| Compound No 15 | 50% |
| Mineral oil | 2% |
| China clay | 48% |

EXAMPLE 9

A dustable powder is prepared by grinding and mixing the active ingredient with talc.

| Compound No 15 | 5% |
| Talc | 95% |

EXAMPLE 10

A suspension concentrate is prepared by ball milling the ingredients to form an aqueous suspension.

| | |
|---|---|
| Compound No 15 | 40% |
| Sodium lignosulphonate | 10% |
| Bentonite clay | 1% |
| Water | 49% |

This formulation can be used as a spray by diluting with water or applied directly to seed.

EXAMPLE 11

A wettable powder formulation is made by mixing and grinding the ingredients until all are thoroughly mixed.

| | |
|---|---|
| Compound No 15 | 25% |
| Sodium laurylsulphate | 2% |
| Sodium lignosulphonate | 5% |
| Silica | 25% |
| China clay | 43% |

EXAMPLE 12

The compounds were tested against a variety of foliar fungal diseases of plants. The technique employed was as follows.

The plants were grown in John Innes Potting Compost (No. 1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient) were sprayed on to the foliage and applied to the roots of the plants in the soil. The sprays were applied to maximum retention and the root drenches to a final concentration equivalent to approximately 40 ppm a.i./dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:

4 = no disease
3 = trace-5% of disease on untreated plants
2 = 6-25% of disease on untreated plants
1 = 26-59% of disease on untreated plants
0 = 60-100% of disease on untreated plants The results are shown in Table III.

TABLE III

| COMPOUND NO | PUCCINIA RECONDITA (WHEAT) | ERYSIPHE GRAMINIS (BARLEY) | VENTURIA INAEQUALIS (APPLE) | PYRICULARA ORYZAE (RICE) | CEROCOSPORA ARACHIDICOLA (PEANUT) | PLASMOPARA VITICOLA (VINE) | PHYTOPHTHORA INFESTANS (TOMATO) |
|---|---|---|---|---|---|---|---|
| 1 | 0 | 3 | 3 | 0 | 4 | 0 | 0 |
| 15 | 4 | 4 | 4 | 4 | 4 | 4 | 4* |
| 16 | 4 | 4 | 4 | 4 | 4 | 4 | 3 |
| 18 | 1 | 4 | 4 | 0 | 4 | 4 | 0 |
| 19 | 4 | 4 | 4 | 4 | 4 | 4 | 0 |
| 20 | 4 | 4 | 4 | 4 | 4 | 4 | 0 |
| 21 | 4 | 4 | 4 | 0 | 4 | 4 | 3 |
| 23 | 4 | 4 | 4 | 4 | 4 | 4 | 4 |
| 57 | 4 | 4 | 4 | 4 | 4 | 4 | 3 |
| 58 | 4 | 4 | 4 | 4 | 4 | 4 | 3 |
| 60 | 4 | 4 | 4 | 4 | 4 | 4 | 4 |
| 66 | 0 | 4 | 4 | 0 | 1 | 2 | 0 |
| 87 | 3 | 4 | 4 | 4 | 4 | 0 | 0 |
| 88 | 4 | 4 | 4 | 2 | 3 | 4 | 4 |
| 106 | 0 | 4 | 0 | 0 | 0 | 0 | — |

*100 ppm root drench only

EXAMPLE 13

This example illustrates the plant growth regulating properties of compounds 15, 16, 19, 20, 23 and 43 of Table I.

These compounds were tested on a whole plant screen for plant growth regulating activity against six species of plant. The plant species used in this screen are presented in Table IV with the leaf stage at which they were sprayed.

A formulation of each chemical was applied at 4000 ppm (4 kg/ha in a 1000 l/ha field volume) using a track-sprayer and a SS8004E (Teejet) nozzle. Additional tests were done on tomatoes at 2000 and 500 ppm.

After spraying, the plants were grown in a glasshouse with 25° C. day/22° C. night temperatures. The exceptions to this were the temperate cereals wheat and barley, which were grown in 13°-16° C. day/11°-13° C. night temperatures. Supplementary lighting was supplied when necessary to provide an average photoperiod of 16 hours (14 hours minimum).

After 2-6 weeks in the glasshouse, depending on species and time of year, the plants were visually assessed for morphological characteristics against a control plant sprayed with a blank formulation. The results are presented in Table V.

TABLE IV

| PLANT MATERIAL USED FOR WHOLE PLANT SCREEN | | | | |
|---|---|---|---|---|
| Species | Code | Variety | Growth Stage at Treatment | No plants per 3" pot | Compost Type |
| Barley | BR | Atem | 1-1.5 leaves | 4 | JIP* |

TABLE IV-continued
PLANT MATERIAL USED FOR WHOLE PLANT SCREEN

| Species | Code | Variety | Growth Stage at Treatment | No plants per 3" pot | Compost Type |
|---|---|---|---|---|---|
| Wheat | WW | Timmo | 1–1.5 leaves | 4 | JIP |
| Maize | MZ | Earliking | 2¼–2½ leaves | 1 | PEAT |
| Apple | AP | Red Delicious | 4–5 leaves | 1 | JIP |
| Rice | RC | Ishikari | 2–2½ leaves | 4 | JIP |
| Tomato | TO | Ailsa Craig | 2–2½ leaves | 1 | PEAT |

*John Innes Potting Compost.

TABLE V

| Compound No | Table | BR | WW | RC | AP | MZ | TO | TO* | TO+ |
|---|---|---|---|---|---|---|---|---|---|
| 5 | I | | | | I | | NT | NT | NT |
| 16 | I | NT | | NT | NT | | NT | NT | NT |
| 19 | I | NT | | NT | NT | | 2GAT | NT | 1 |
| 20 | I | NT | NT | NT | NT | NT | NT | 1 | |
| 23 | I | NT | IG | NT | NT | | I | 1 | 2G |
| 43 | I | 2T | T | T | | I | G | NT | 1 |

KEY
*2000 ppm
+500 ppm
Retardation 1–3 where
1 = 10–30%
2 = 21–60%
3 = 61–100%
Green effect = G
Apical damage = A
Tillering or side shooting = T
Blank means less than 10% effect
NT indicates that the compound was not tested against this species.

We claim:

1. A compound having the general formula (I):

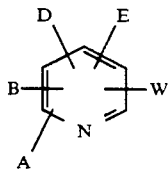

and stereoisomers thereof, wherein W, which is attached to the pyridine ring at the 2-, 3- or 4-position, is $R^1O_2C-C=CH-ZR^2$, wherein $R^1$ and $R^2$, which are the same or different, are $C_{1-6}$alkyl or fluoro $(C_{1-6})$alkyl groups, and Z is either an oxygen or sulphur atom; A is pyrimidinyloxy, pyrimidinylthio, pyrimidinyloxyalkyl, pyrazinyloxy or pyrazinylthio; B, D and E, which are the same or different, are hydrogen or halogen atoms, or hydroxy, $C_{1-6}$alkyl optionally substituted with halogen, hydroxy, alkoxy or phenoxy, $C_{1-6}$alkoxy, phenyl $(C_{1-6})$alkyl, phenyl $(C_{1-6})$alkoxy, $C_{2-6}$alkenyl optionally substituted with phenyl, $C_{2-6}$alkynyl, phenyl, phenoxy, phenylthio, —NR'R", —NHCOR', —OCOR' (in which R' and R" are as defined below), phenylazo, nitro cyano, —$CO_2R^3$, —$CONR^3R^4$, —$COR^3$, —$CR^3NR^4$, N=$CR^3R^4$ or —$S(O)_nR^3$ groups; n is 0, 1 or 2; and $R^3$ and $R^4$, which are the same or different, are hydrogen atoms or $C_{1-6}$alkyl, $C_{3-6}$cycloalkyl, $C_{3-6}$cycloalkyl($C_{1-4}$)alkyl, $C_{2-6}$alkenyl, $C_{2-6}$alkynyl, phenyl or phenyl ($C_{1-6}$)alkyl groups; any foregoing aryl moiety or the pyrimidinyl or pyrazinyl ring of A being optionally substituted with one or more of halogen, hydroxy, $C_{1-4}$alkyl, $C_{1-4}$alkoxy, halo($C_{1-4}$)alkyl, halo($C_{1-4}$)alkoxy, $C_{1-4}$alkylthio, ($C_{1-4}$)alkyl, phenyl, phenoxy, phenyl($C_{1-4}$)alkyl, phenyl($C_{1-4}$)alkoxy, phenoxy($C_{1-4}$)alkyl, acetyloxy, benzoyloxy, cyano, thiocyanato, nitro, —NR'R", —NHCOR', —NHCONR'R", —CONR'R", —COOR', —$OSO_2R'$, —$SO_2R'$, —COR', —CR'=NR" or —N=CR'R" in which R' and R" are independently hydrogen, $C_{1-4}$alkyl, $C_{1-4}$alkoxy, $C_{1-4}$alkylthio, $C_{3-6}$cycloalkyl, $C_{3-6}$cycloalkyl ($C_{1-4}$)alkyl, phenyl or benzyl, the phenyl and benzyl groups being optionally substituted with halogen, $C_{1-4}$alkyl or $C_{1-4}$alkoxy; and metal complexes thereof.

2. A compound according to claim 1 in which A is pyrimidinyloxy.

3. A compound according to claim 1 in which A is ortho to W.

4. A compound according to claim 1 in which A and W are in the 2- and 3-positions, respectively, of the pyridine ring.

5. A compound according to claim 1 in which B, D and E are all hydrogen.

6. A compound according to claim 1 in which $R^1$ and $R^2$ are both methyl.

7. A compound according to claim 1 in which Z is oxygen.

8. A compound having the formula (II):

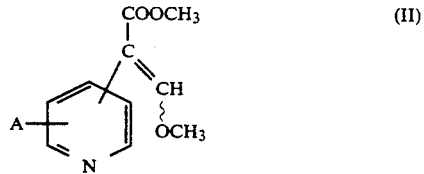

wherein A, which is in a position ortho to the acrylate group, is pyrimidinyloxy-, pyrimidinylthio, pyrazinyloxy or pyrazinylthio (each optionally substituted with chloro, bromo or trifluoromethyl).

9. The (E)-isomer of a compound according to claim 1.

10. A fungicidal composition comprising, as an active ingredient, a compound according to claim 1 and a fungicidally acceptable carrier or diluent therefor.

11. A method of combating fungi which comprises applying to a plant or seed or to a locus thereof an effective amount of a compound to claim 1.

12. An insecticidal/nematocidal composition comprising an insecticidal/nematocidal compound of formula (I) according to claim 1 and a carrier or diluent therefor.

13. A method for killing or controlling insect and nematode pests which comprises administering to the insect or nematode or to a locus thereof an effective amount of an insecticidal/nematocidal compound of formula (I) as defined in claim 1.

14. A plant growth regulator composition comprising a plant growth regulating compound of formula (I) according to claim 1 and a carrier or diluent therefor.

15. A method of regulating plant growth which comprises applying to a plant or seed of a plant or a locus thereof an effective amount of a plant growth regulating compound of formula (I) according to claim 1.

* * * * *